US012575948B2

(12) United States Patent
Bartlett et al.

(10) Patent No.: US 12,575,948 B2
(45) Date of Patent: Mar. 17, 2026

(54) PROSTHETIC FOOT WITH DISTRIBUTED STRESS

(71) Applicant: Little Room Innovations, LLC, Ann Arbor, MI (US)

(72) Inventors: Harrison Logan Bartlett, Atlanta, GA (US); Brian Edward Lawson, Ann Arbor, MI (US); Lowell D. Jones, Franklin, TN (US); Michael Goldfarb, Franklin, TN (US)

(73) Assignee: Little Room Innovations, LLC, Ann Arbor, MI (US)

( * ) Notice: Subject to any disclaimer, the term of this patent is extended or adjusted under 35 U.S.C. 154(b) by 491 days.

(21) Appl. No.: 18/026,736

(22) PCT Filed: Sep. 16, 2021

(86) PCT No.: PCT/US2021/050673
§ 371 (c)(1),
(2) Date: Mar. 16, 2023

(87) PCT Pub. No.: WO2022/060985
PCT Pub. Date: Mar. 24, 2022

(65) Prior Publication Data
US 2024/0009006 A1 Jan. 11, 2024

Related U.S. Application Data

(60) Provisional application No. 63/079,754, filed on Sep. 17, 2020.

(51) Int. Cl.
*A61F 2/66* (2006.01)
*A61F 2/50* (2006.01)

(52) U.S. Cl.
CPC ........ *A61F 2/66* (2013.01); *A61F 2002/5056* (2013.01); *A61F 2002/509* (2013.01); *A61F 2002/665* (2013.01); *A61F 2002/6657* (2013.01)

(58) Field of Classification Search
CPC ............... A61F 2/66; A61F 2002/5056; A61F 2002/665; A61F 2002/6657;
(Continued)

(56) References Cited

U.S. PATENT DOCUMENTS 5,549,711 A      8/1996  Bryant
8,808,395 B2 *   8/2014  Townsend ................. A61F 2/66
                                                    623/47
(Continued)

OTHER PUBLICATIONS

International Search Report and Written Opinion dated Dec. 27, 2021 in International Application No. PCT/US2021/050673 (7 pages).
(Continued)

*Primary Examiner* — Bruce E Snow
(74) *Attorney, Agent, or Firm* — Robinson IP Law, PLLC

(57) ABSTRACT

A prosthetic foot includes a spring component and a sole component. The spring component comprises two or more stacked beam elements, each beam element including, along the length of the respective beam element, a first portion and a second portion, and the second portion of the beam element includes an extent with a length-varying width. The respective beam elements are fixed to each other and to the sole component proximate the heel portion of the sole component or the toe portion of the sole component at the first portions of the respective beam elements to form a fixed end of a cantilevered composite beam. The second portions of the respective beam elements are laterally movable with respect to each other when the spring component deflects.

12 Claims, 15 Drawing Sheets

(58) Field of Classification Search
CPC ........ A61F 2002/502; A61F 2002/5021; A61F
2002/5024; A61F 2002/5055; F16F 1/368
See application file for complete search history.

(56) References Cited

U.S. PATENT DOCUMENTS

| | | |
|---|---|---|
| 10,390,974 B2 | 8/2019 | Clausen et al. |
| 2005/0187640 A1 | 8/2005 | Christensen |
| 2010/0023135 A1 | 1/2010 | Rubie et al. |
| 2012/0179274 A1* | 7/2012 | Christensen .............. A61F 2/66 623/55 |
| 2019/0125552 A1 | 5/2019 | Day et al. |
| 2024/0009006 A1* | 1/2024 | Bartlett .................... A61F 2/66 |

OTHER PUBLICATIONS

YouTube, "Lecture 33 Introduction to Assistive Devices for Mobility", (NPTEL-NOC IITM), May 6, 2019, retrieved from URL: https://www.youtube.com/watch?v=MyW6Hpekfio&t=601s (1 page).
M.A. Osipenko et al., "Mathematical Modeling of the Foot Prosthesis Elastic Element Under Bending", Russian Journal of Biomechanics, vol. 5, No. 2, 2001, pp. 18-29 (12 pages).
D. Spreemann, B. Folkmer, and Y. Manoli, "Realization of nonlinear hardening springs with predefined characteristic for vibration transducers based on beam structures," in MikroSystemTechnik Kongress, Darmstadt, Deutschland, 2011 (4 pages).

* cited by examiner

PROSTHETIC FOOT WITH DISTRIBUTED STRESS

CROSS REFERENCE TO RELATED APPLICATIONS

This application is a 35 U.S.C. § 371 National Stage of International Patent Application No. PCT/US2021/050673 filed Sep. 16, 2021, which claims the benefit under 35 U.S.C. § 119(e) of the filing date of U.S. Provisional Patent Application No. 63/079,754 filed Sep. 17, 2020, the contents of which are hereby incorporated by reference in their entirety.

This invention was made with government support under Grant Number R44HD096967 awarded by the National Institutes of Health (Eunice Kennedy Shriver National Institute of Child Health & Human Development). The government has certain rights in the invention.

FIELD OF THE DISCLOSURE

This disclosure relates to a prosthetic foot incorporating a composite spring component including a stack of beam elements.

BACKGROUND

Many current prosthetic feet may be classified as energy storage and release (ESR) devices. Such feet provide multiple benefits to their users. Namely, these ESR feet are able to support the weight of the user when standing and walking, provide an appropriate motion to the shank body segment when walking, cushion impact during heel strike, and store and release energy during the stance phase of walking (i.e., the phase of gait during which the foot is in contact with the ground). Additionally, due to the high loads on the foot associated with walking and the long desired lifetime of a prosthetic device, ESR feet must be very durable. ESR feet are often designed as cantilevered spring-like structures, and they are typically made from composite materials. This spring-like construction provides the aforementioned functionality with a relatively simple design.

Current ESR prosthetic feet are designed as curved beam structures with approximately constant thickness along their length. Because prosthetic feet are mourned to the shank body segment (residual or artificial limb) and are primarily loaded at the ball of the foot, and due to the beam-like design of ESR feet, current ESR feet may be roughly modeled as simple cantilevered beams. In a simple cantilevered beam model, stress is concentrated at the outside edges of the fixed end of the beam when loaded. Specifically, the free end of the beam carries little stress, while the fixed end of the beam is under considerable stress, particularly at the surface of the beam. This stress concentration is illustrated in the grayscale stress distribution shown in FIG. 1 which depicts a side view (sagittal plane) of a cantilevered beam stress distribution (wherein the lighter the shade, the greater the stress). Due to the similar form of current ESR prosthetic feet and simple cantilevered beams, this stress concentration is present in current prosthetic feet.

The stress concentration associated with current prosthetic devices' construction elucidates multiple drawbacks associated with current foot design approaches. Due to the need for compliant, spring-like, foot designs, simple cantilevered beam type prosthetic feet must have a large effective cantilever length to provide the appropriate compliance when loaded without exceeding stress limits. As such, many simple cantilever beam type prosthetic feet adopt curved shapes (generally "J" or "C" shaped devices) and are relatively large (tall build height) to obtain the necessary beam length for the desired compliance. This tall build height may preclude patients with long residual limbs from using such a device.

Additionally, due to the long beam length and associated device size, these simple cantilever beam type devices may be heavier than what is required to achieve their given stiffness. This fact is a significant drawback, as minimizing weight is one of the most important factors for many prosthesis users. The stress concentration present in simple cantilevered beam type ESR foot designs poses an additional problem associated with energy storage. Specifically, strain energy is stored in regions of a beam that are under significant stress. Due to the stress concentration in simple cantilevered beams, energy is primarily stored in the region of the beam that is under this high stress. As such, other regions of the beam (such as the beam tip) store little energy, and as a result, the energy storage density of the beam is relatively low. The strain energy density of a material is defined as the energy that is stored in the material per unit volume at a given level of stress. This strain energy density, $\rho_\epsilon$, can be expressed mathematically as follows where $\sigma$ is the material stress and E is the material's elastic modulus (1).

$$\rho_\epsilon = \frac{\sigma^2}{2E} \tag{1}$$

As the name suggests, ESR feet aim to store and return significant energy during the stance phase of gait. To store and return significant amounts of energy while simultaneously maintaining a small design envelope, a design with higher strain energy density should be considered for prosthetic feet.

Some patients requiring prosthetic feet have long residual limbs. To provide these patients with prosthetic feet, the feet must be designed with a low build height. As previously discussed, simple cantilever beam prosthetic feet may be curved and have generally tall build heights to provide the appropriate compliance without exceeding stress limits. Prosthetic feet made for patients with long residual limbs generally have low compliance (i.e. are stiff) to fit within the allotted build volume while not exceeding material stress limits. As such, devices available to patients with long residual limbs generally do not have the desirable compliant behavior of taller prosthetic devices.

Simple cantilever beam type ESR prosthetic feet are generally curved beams constructed from composite materials such as carbon fiber, fiberglass, or Kevlar. The manufacturing process for such devices may be difficult due to the custom composite material layups and complicated fixturing procedures. As such, the manufacturing process for these ESR prosthetic feet may be both time consuming and costly. Additionally, the final product cannot be easily modified by a clinician to meet a patient's needs. Currently available prosthetic devices do not generally incorporate any methods for patient-specific customization of the dynamic properties of the foot. Instead, devices are made available in discrete sizes and stiffnesses, and a clinician must select one of these options for their patient with little to no customization potential.

Many prosthesis manufacturers of ESR prosthetic feet mitigate the stress concentration present in simple cantilevered beam designs by tapering their feet in the thickness dimension. Such an approach necessitates custom lay-up techniques for producing the spring component from composite materials. The result is a highly specialized ESR foot that is relatively expensive to fabricate when compared to standard flat-plate composite lay-ups. Additionally, this tapered spring design approach also results in a foot with less-than-optimal energy storage capacity. The maximum stress in the beam will occur at the surface of the structure and will decrease linearly to zero from the surface of the beam to the neutral axis. As such, in the thick regions of a tapered beam, the material near the neutral axis will not be subject to significant stress, and therefore, will store and return little energy (relative to the device volume).

Therefore, there is a need for a prosthetic foot design that, when loaded, distributes stress more evenly throughout the foot structure. Preferably, the design would not complicate design factors related to composite lay-ups (i.e., does not taper the thickness of the material). Such a design would allow for smaller and lighter devices with increased durability, decreased stiffness, and increased energy storage potential, but also preserve simplicity and versatility, making replacement prostheses cheaper. Additionally, there is a need for a foot with the potential for patient-specific customization to be performed by a clinician. Such a design has the potential to make foot repair relatively simple, possibly even allowing users (i.e., soldiers in the field) to replace worn or broken spring elements without the aid of a clinician. Other applications include pediatric use, as the lower cost and ease of replaceability would facilitate the many adjustments and stiffness substitutions necessary for a growing child.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

Aspects of the disclosure include a prosthetic foot including a spring component and a sole component. The spring component may include two or more stacked beam elements. Each beam element includes, along the length of the respective beam element, a first portion and a second portion. The second portion of each beam element includes an extent with a length-varying width. The respective beam elements are fixed to each other and to the sole component at the first portions of the respective beam elements, and the second portions of the respective beam elements are laterally movable with respect to each other when the spring component deflects.

According to further aspects of the disclosure, the spring component may form a beam of uniform strength.

According to further aspects of the disclosure, the summed width of the two or more stacked beam elements may increase approximately linearly from a second end of the spring component to a first end of the spring component.

According to further aspects of the disclosure, the two or more beam elements may be of varying lengths.

According to further aspects of the disclosure, the two or more stacked beam elements may be flat plates.

According to further aspects of the disclosure, the two or more stacked beam elements may be curved laterally.

According to further aspects of the disclosure, the two or more stacked beam elements may be curved longitudinally.

According to further aspects of the disclosure, the prosthetic foot may include a shank connector connected to the spring component where the respective beam elements are fixed to each other and to the sole component and wherein a free end of the spring component extends toward a toe portion of the sole component.

According to further aspects of the disclosure, the spring component may form a cantilevered beam constructed and arranged so as to distribute maximum stress approximately uniformly along its length when substantially loaded at a free end of the cantilevered beam.

According to further aspects of the disclosure, the beam elements may have approximately constant thicknesses along their lengths.

According to further aspects of the disclosure, the prosthetic foot may include a shank connector. The respective beam elements are fixed to each other and to the sole component at or near a toe portion of the sole component, and the shank connector is connected to a free end of the spring component at or near a heel portion of the sole component.

According to further aspects of the disclosure, the prosthetic foot may include low friction coatings, elastomeric bearings, or low friction materials between overlapping beam elements.

According to further aspects of the disclosure, each of the beam elements includes an arch in a transverse plane.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

DETAILED DESCRIPTION

Figure 1:
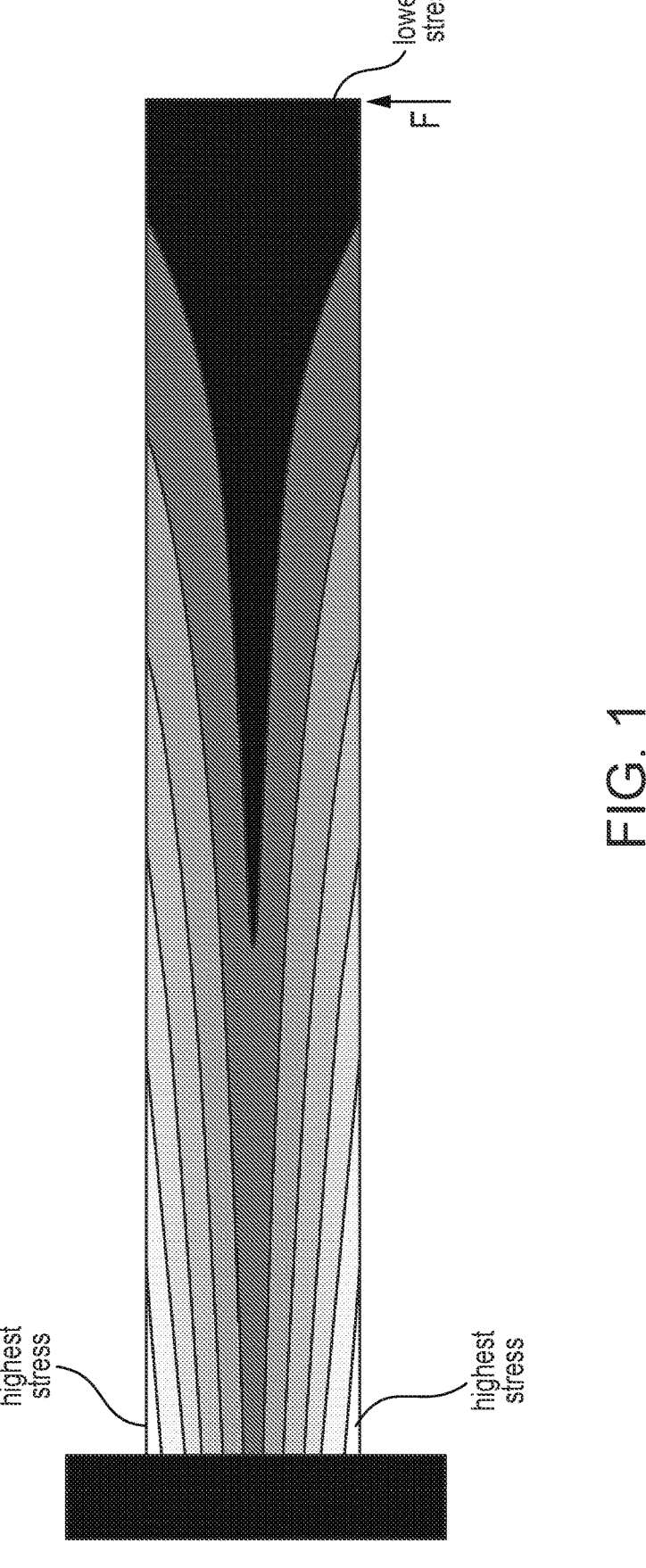
FIG. 1 shows a simple cantilevered beam side view with stress distribution shown as grayscale.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Definitions

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use various terms describing relative spatial arrangements and/or orientations or directions in describing the position and/or orientation of a component, apparatus, location, feature, or a portion thereof or direction of movement, force, or other dynamic action. Unless specifically stated, or otherwise dictated by the context of the description, such terms, including, without limitation, top, bottom, above, below, under, on top of, upper, lower, left, right, in front of, behind, beneath, next to, adjacent, between, horizontal, vertical, diagonal, longitudinal, transverse, radial, axial, clockwise, counter-clockwise, etc., are used for convenience in referring to such component, apparatus, location, feature, or a portion thereof or movement, force, or other dynamic action in the drawings and are not intended to be limiting.

Unless otherwise indicated, or the context suggests otherwise, terms used herein to describe a physical and/or spatial relationship between a first component, structure, or portion thereof and a second component, structure, or portion thereof, such as, attached, connected, fixed, joined, linked, coupled, or similar terms or variations of such terms, shall encompass both a direct relationship in which the first component, structure, or portion thereof is in direct contact with the second component, structure, or portion thereof or there are one or more intervening components, structures, or portions thereof between the first component, structure, or portion thereof and the second component, structure, or portion thereof.

Unless otherwise stated, any specific dimensions mentioned in this description are merely representative of an exemplary implementation of a device embodying aspects of the disclosure and are not intended to be limiting.

To the extent used herein, the terms "about" or "approximately" apply to all numeric values and terms indicating specific physical orientations or relationships such as horizontal, vertical, parallel, perpendicular, concentric, or similar terms, specified herein, whether or not explicitly indicated. This term generally refers to a range of numbers, orientations, and relationships that one of ordinary skill in the art would consider as a reasonable amount of deviation to the recited numeric values, orientations, and relationships (i.e., having the equivalent function or result) in the context of the present disclosure. For example, and not intended to be limiting, this term can be construed as including a deviation of ±10 percent of the given numeric value, orientation, or relationship, provided such a deviation does not alter the end function or result of the stated value, orientation, or relationship. Therefore, under some circumstances as would be appreciated by one of ordinary skill in the art, a value of about or approximately 1% can be construed to be a range from 0.9% to 1.1%.

As used herein, the term "adjacent" refers to being near (spatial proximity) or adjoining. Adjacent objects can be spaced apart from one another or can be in actual or direct contact with one another. In some instances, adjacent objects can be coupled to one another or can be formed integrally with one another.

As used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as stated as well as instances in which the event, circumstance, characteristic, or properly occurs to a close approximation, such as accounting for typical tolerance levels or variability of the embodiments described herein.

As used herein, the term "beam of uniform strength," "uniform strength beam," or similar term means a beam in which bending stress is substantially, or about, uniform along the length of the beam, which may be achieved by varying the width of the beam and keeping the thickness constant, varying the thickness of the beam and keeping the width constant, or some combination thereof.

All possible combinations of elements and components described in the specification or recited in the claims are contemplated and considered to be part of this disclosure. It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Description of Exemplary Embodiments

To address many issues associated with both simple cantilevered beam type and thickness-tapered type ESR prosthetic foot designs, the stress concentration inherent to its construction can be distributed more evenly across the foot structure. In a cantilevered beam, the stress $\sigma$ at any given point (x, y) in the beam is defined by (2) where M is the applied moment experienced at a distance x along the beam, y is the vertical distance to the point of interest from the neutral axis, and I is the second moment of area of the beam at a cross section located at a distance x along the beam.

$$\sigma(x, y) = \frac{-M(x)y}{I(x)} \quad (2)$$

In a simple cantilevered beam construction, the moment increases linearly from the free end to the fixed end of the beam while the second moment of area remains constant across the length of the beam. As such, the maximum stress occurs at the fixed end of the beam where the moment is maximized. To distribute stress more evenly across the length of the beam, the beam shape may be made to change along its length to increase the second moment of area, I, as the moment, M, simultaneously increases. More advantageously, the beam may be designed such that the stress in the beam is no longer a function of the distance along the length of beam, x. In such a beam, maximum stress experienced by the beam is uniform along the entire length of the beam and occurs at the outer surface of the beam (where y is maximum). Beams shaped in this way are known as beams of uniform strength.

Several different beam shapes can achieve this property of uniform maximum stress along the length of the beam. To distribute the maximum stress in the beam uniformly across both the length and width of the beam, beam shapes should be selected with a flat top and bottom surface such that the maximum value of y (and, therefore the maximum value of $\sigma$) is constant across the width of any cross section. As a simplifying assumption, we provide a detailed discussion here for only beams with rectangular cross sections. However, examples described herein also consider beams of uniform maximum stress along their length with non-rectangular cross sections. In beams of uniform strength with rectangular cross sections, both the beam width and thickness may vary as a function of distance along the length of the beam (x).

Two different beams of uniform strength are considered in more detail: 1) a beam of constant width and varying thickness, and 2) a beam of varying width and constant thickness. Although these two beam variants are considered here in more detail, it is also possible to design a beam of uniform strength with varying thickness and varying width. Such a beam could be used to design a spring component for a prosthetic foot.

In a beam of uniform strength with constant width, the thickness of the beam may be tapered in a specific way along the length of the beam such that the maximum stress is uniformly distributed along the length of the beam when loaded. The shape of the outer surface of the beam will follow the shape of a square root function from the free end to the fixed end, where the free end thickness is zero. It is then possible to design a cantilevered spring component for a prosthetic foot from a beam of uniform strength and constant width, Such a beam of uniform strength and constant width may be shaped (i.e. bent) into the form of the prosthetic foot.

Figure 2:
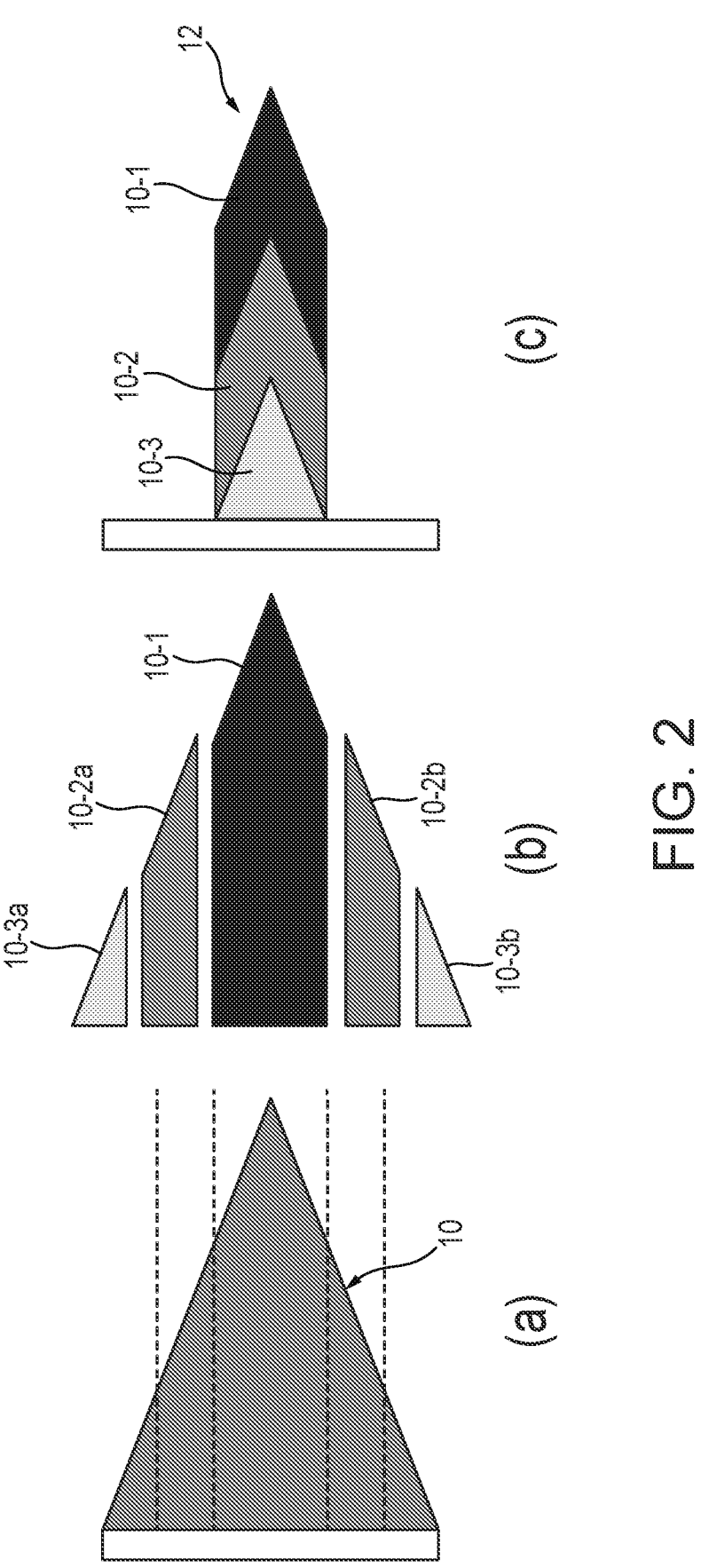
FIG. 2(a) is a top plan view of a beam of constant thickness with varying width and uniform strength.
FIG. 2(b) is a top plan view of the beam of FIG. 2(a) with the beam virtually segmented.
FIG. 2(C) is a top plan view of a beam with stacked segments of FIG. 2(b) forming a composite beam of uniform strength.

In a beam of uniform strength with constant thickness, the width of the beam varies to form a triangularly shaped plate with the tip of the triangle being loaded (loaded orthogonally to the plane of the triangle) and the base being fixed. This triangularly shaped plate may then be virtually segmented into strips and stacked on top of one another to form a composite beam made of layered plates. This composite beam design process is illustrated in FIGS. 2(a), (b) and (c). This composite beam structure will retain the uniform strength properties of the original triangularly shaped plate. FIG. 2(a) is a top view of a beam 10 of uniform strength having a triangular shape with a length-varying (decreasing) width from the fixed (left-hand) end to the free (right-hand) end. If the triangular beam 10 were sliced along the dashed lines in FIG. 2(a) to produce segments 10-1, 10-2b, 10-3a, and 10-3b shown in FIG. 2(b), and those segments were combined as shown in FIG. 2(c), the resulting composite beam 12 would also be a beam of uniform strength. Segments 10-2a and 10-2b are not necessarily separate pieces, but could be two halves of a continuous middle beam. Similarly, segments 10-3a and 10-3b are not necessarily separate pieces, but could be two halves of a continuous middle beam. In any event, the summed widths of the bottom beam 10-1, the middle beam comprising segments, or halves, 10-2a and 10-2b, and the top beam comprising segments, or halves, 10-3a and 10-3b, increase approximately linearly from the right tip of composite beam 12 to the left base of composite beam 12. In this regard, the term "approximately linearly"—or "about linearly"—means linearly or approximately linearly and continuously or approximately continuously. For example, if the pointed tips of any one of segments 10-1, 10-2 and 10-3 were truncated or removed to form a blunt or rounded tip, the summed width of the segments 10-1, 10-2, and 10-3 would decrease approximately linearly and approximately continuously along the length of the composite beam 12 from the fixed end to the free end.

Figure 3:
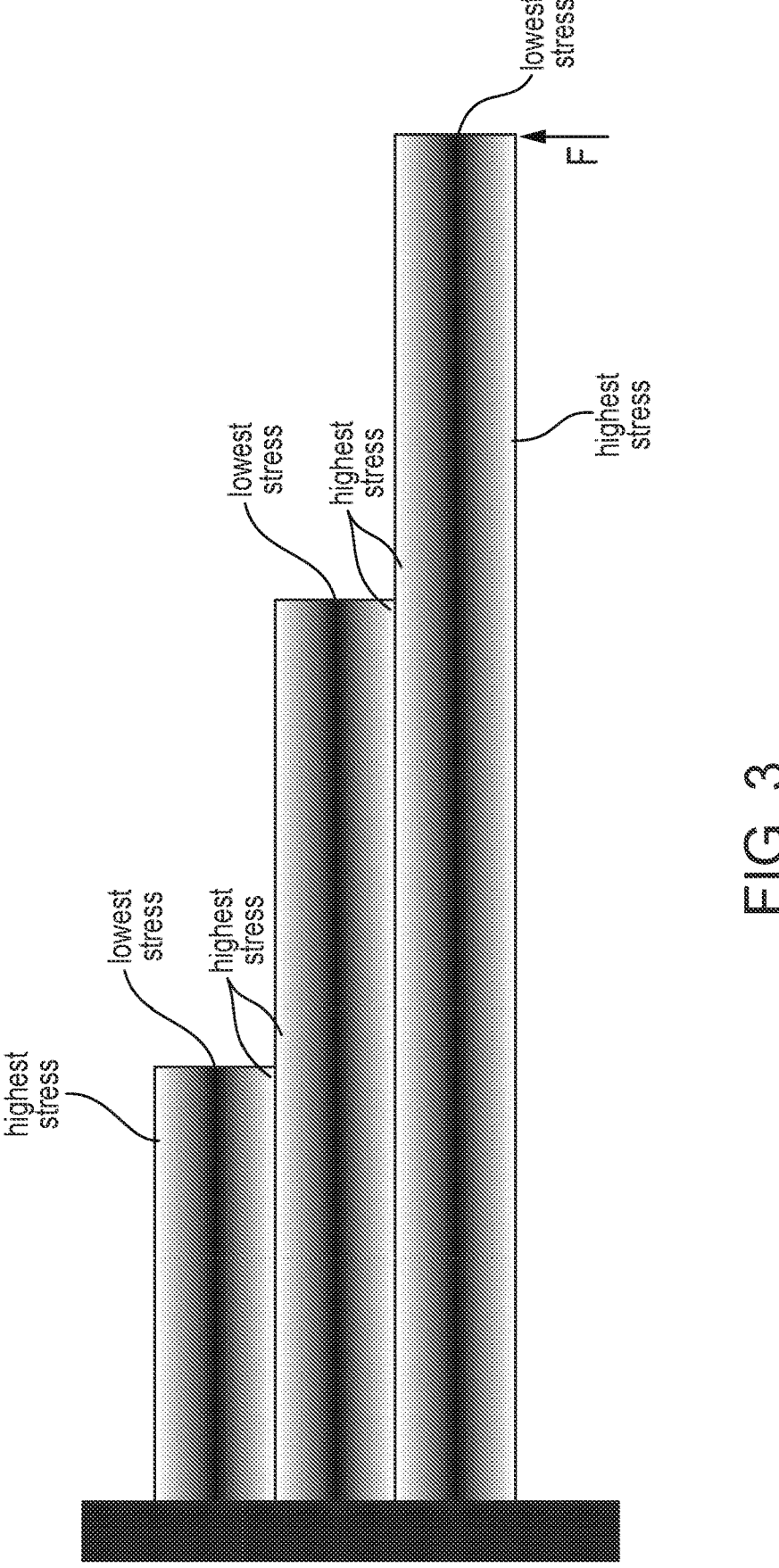
FIG. 3 is a side view of composite beam constructed of three stacked beam elements showing stress distribution, shown as grayscale, for a force F applied at its free end.

This composite beam constructed of stacked beam elements or plates may be designed to have a constant width for a significant portion of its length that is appropriate for a prosthetic foot, even if the triangular beam from which the composite beam originated has a base (fixed end) larger than is practical for a foot (see FIG. 2(c)). Note that, other than at the fixed end, the stacked beam elements can move independently of one another, so that when the beam is loaded, adjacent plate surfaces slide against one another. When loaded, the composite beam 12 will maintain the uniform strength properties of the original triangular shaped beam 10. Specifically, the stress distribution for a composite spring constructed of three stacked beam elements (or layered plates) can be seen in FIG. 3 (wherein, again, the lighter the color, the greater the stress). It should be noted that, for a length of beam, the thickness of the plates as well as number of stacked plates may be modified to change the stiffness properties of the composite beam. It should also be noted that in the beam depicted in FIG. 3, the maximum stress is equal along the length of the composite beam structure and occurs at the opposed surfaces of each of the stacked plates.

In an embodiment, this composite uniform strength beam constructed from layered plates may be implemented in a prosthetic foot. In such an embodiment, the layered plates may be flat or curved into the shape of a foot structure (FIGS. 4-15). Although not pictured, the foot components may have a thin slot cut down the center of the foot to allow for frontal plane foot compliance.

Figure 4:
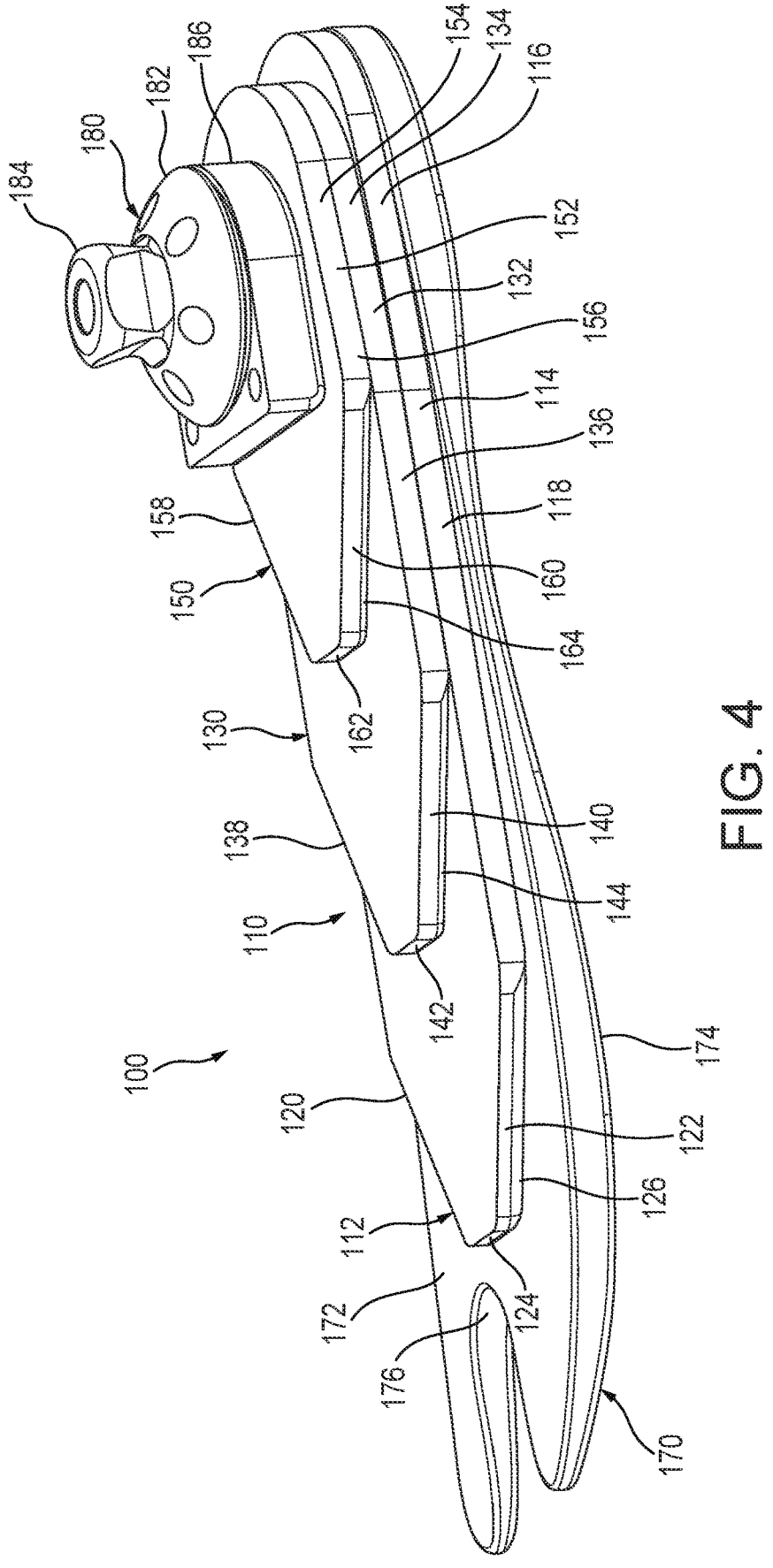
FIG. 4 is a perspective view of a prosthetic foot with composite beam spring component constructed of stacked beam elements (3 plates) acid including a sole component and a standard connector for prosthetic feet.

As shown in FIG. 4, a prosthetic foot 100 includes a stacked plate composite beam, or spring component, 110 secured to a contoured bottom piece, or sole component, 170 and a shank connector (or pyramid connector or pyramid adaptor) 180 connected to a connector mounting fixture, or adaptor plate, 186 that is connected to the composite spring component 110. Shank connector 180 may include a base 182 connected (e.g., by suitable fasteners) to the connector mounting fixture, or adaptor plate, 186 and an extension 184 this is connectable in a known manner to a shank comprising a natural, residual limb or artificial limb portion.

In the illustrated embodiment, stacked plate composite spring component 110 comprises three stacked beam elements, or plates: bottom beam element 112, middle beam element 130, and top beam element 150.

Bottom beam element 112 includes a first portion 114 of its length and a second portion 120 of its length. First portion 114 includes an anchored end 116 at which the bottom beam element 112 is connected to the middle beam element 130, the top beam element 150, and the bottom piece 170 and may include a section or longitudinal extent 118 of generally constant width. Second portion 120 includes a section or longitudinal extent 122 with a length-varying width, which may be linearly or approximately linearly tapered and may have a truncated tip 124. Alternatively, section 122 may extend to a point as with a triangle. The tip may be truncated to avoid a sharp point that may cause injury or be easily breakable, and truncating the tip does not substantially affect the stress distribution properties of the composite spring component 110.

Middle beam element 130 includes a first portion 132 of its length and a second portion 138 of its length. First portion 132 includes an anchored end 134 at which the middle beam element 130 is connected to the bottom beam element 112 and the top beam element 150 and may include a section or longitudinal extent 136 of generally constant width. Second portion 138 includes a section or longitudinal extent 140 with a length-varying width, which may be linearly or approximately linearly tapered and may have a truncated tip 142. Alternatively, section 140 may extend to a point as with a triangle.

Top beam element 150 includes a first portion 152 of its length and a second portion 158 of its length. First portion 152 includes an anchored end 154 at which the top beam element 150 is connected to the middle beam element 130 and the connector mounting fixture, or adaptor plate, 186 and may include a section or longitudinal extent 156 of generally constant width. Second portion 158 includes a section or longitudinal extent 160 with a length-varying width, which may be linearly or approximately linearly tapered and may have a truncated tip 162. Alternatively, section 160 may extend to a point as with a triangle.

The composite spring component 110 may be configured so that the summed widths of the beam elements 112, 130, 150 increase approximately linearly from the free end of the spring component 110 (tip 124 of bottom beam element 112)

to the anchored ends 116, 134, 154 and so that the spring component 110 is a beam of uniform strength.

The contoured bottom piece, or sole component, 170 may include a flat top surface 172 and a contoured bottom surface 174. Bottom piece 170 may further include a toe slot 176.

The stacked composite spring component 110 is secured to the connector mounting fixture 186 and shank connector 180 as well as the bottom piece 170 at the anchored ends 116, 134, 154, of the respective beam elements 112, 130, 150, which are located at substantially the same longitudinal position along the composite spring component 110. In the embodiment, the beam elements 112, 130, 150 are not elsewhere connected to each other or to the bottom piece 170. Accordingly, the composite spring component 110 is effectively a cantilevered beam fixed at the anchored ends 116, 134, 154, and any vertical force applied along the length of the spring component 110 away from the anchored ends will cause a deflection of the spring component 110 whereby portions of the individual beam elements 112, 130, 150 are able to slide with respect to each other.

Figure 5:
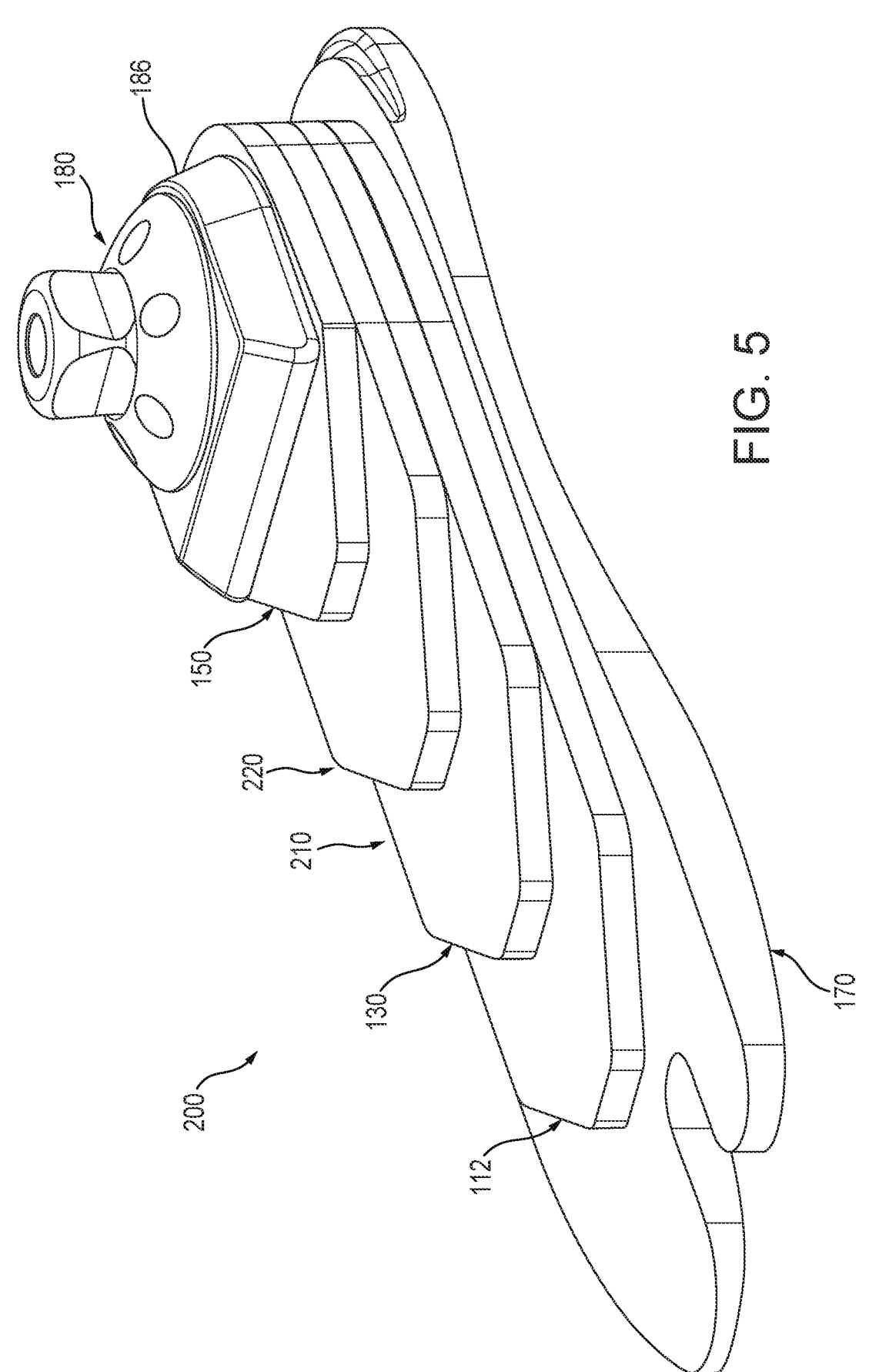
FIG. 5 is a perspective view of a prosthetic foot with composite beam spring component constructed of stacked beam elements (4 plates) and including a sole component.
Figure 6:
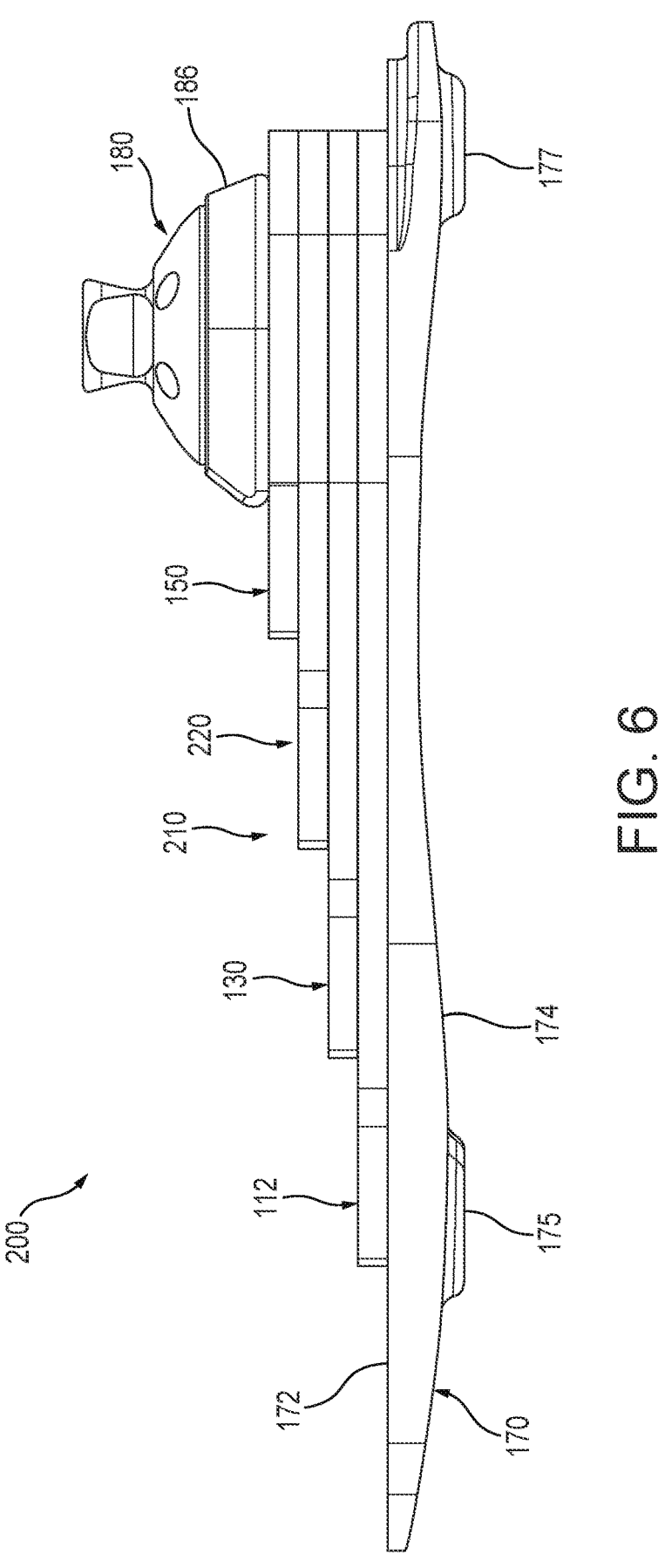
FIG. 6 is a side view of a prosthetic foot of FIG. 5.
Figure 7:
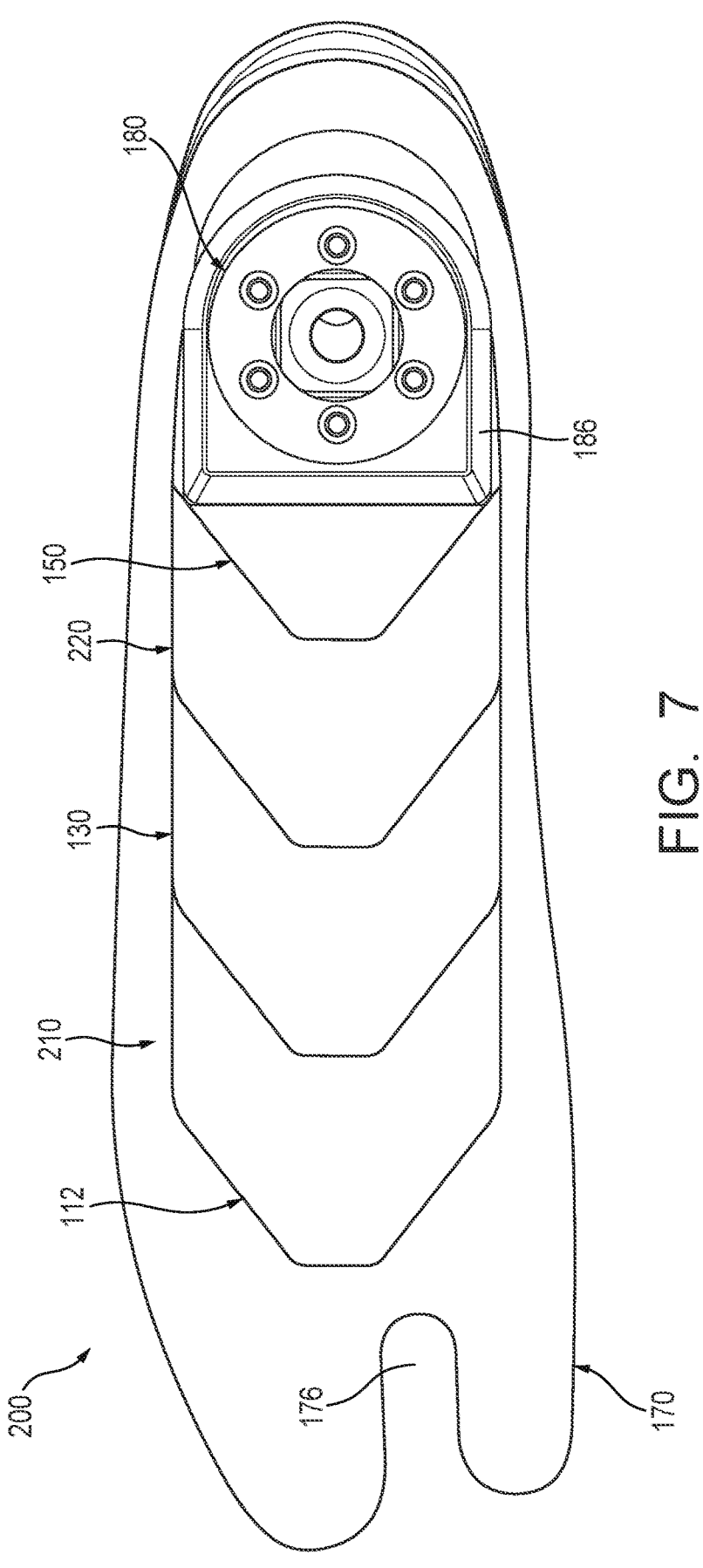
FIG. 7 is a top, plan view of a prosthetic foot of FIG. 5.

In the example shown in FIG. 4, spring component 110 has three beam elements, 112, 130, 150. The composite spring component may have any number of two or more beam elements. FIGS. 5-7 illustrate an alternate example of a prosthetic foot 200 having a composite spring component 210 that includes an additional, intermediate beam element 220 between top beam element 150 and middle beam element 130.

As noted earlier, in the case of the composite uniform strength beam constructed from stacked beam elements, as the load on the composite uniform strength beam changes and the composite spring deflects, portions of the beam elements of the composite spring away from the anchored points may slide past each other. To reduce wear due to this sliding, various approaches may be utilized to accommodate this sliding behavior. For example, in various embodiments, the length-varying width portion 122 of the bottom beam element 112 may have beveled edges 126, the length-varying width portion 140 of the middle beam element 130 may have beveled edges 144, and the length-varying width portion 160 of the top beam element 150 may have beveled edges 164 to prevent one beam element from scoring the adjacent beam element as the beam elements slide relative to each other. In another example, low friction coatings or lubricants may be applied to the beam elements of the composite spring. Low friction materials, such as PTFE (Teflon®), may also be placed between the beam elements of the composite spring to reduce forces due to friction. Alternatively, a material may be placed between the beam elements of the composite spring with a relatively low shear modulus. For example, an elastomer may be placed between beam elements of the composite spring to deform laterally and to serve as elastomeric bearing as adjacent beam elements move laterally with respect to each other during beam deflection. In this example, the elastomer undergoes deformations in shear, and the friction forces between the beam elements of the composite spring are eliminated. Methods to change the frictional behavior between the beam elements of the composite spring are not limited to those listed above.

In an embodiment of the composite beam design approach constructed from layered, or stacked, plates, or beam elements, a desired nonlinear stiffness behavior may be designed into the prosthetic foot. For example, the prosthetic foot's stiffness may be made to increase or decrease as the load at the end of the composite beam increases. Biomechanically, it may be advantageous for the foot stiffness to increase with load as observations from healthy biomechanical data indicate that human ankle stiffness increases with load. To mimic normative biological function, it may be advantageous to design a prosthetic foot with an increasing spring rate. Alternatively, it may be advantageous for the prosthetic foot stiffness to decrease as loading increases. Springs with decreasing spring rates (softening springs) are able to store more energy than a linear spring (or stiffening spring) for an equivalent maximum load. As such, a prosthetic foot with a foot stiffness that decreases as loading increases may provide more energy storage and return relative to a foot with a linear stiffness (or one with an increasing stiffness). This increased energy return may help to reduce the metabolic cost of walking with a prosthetic foot.

Figure 8:
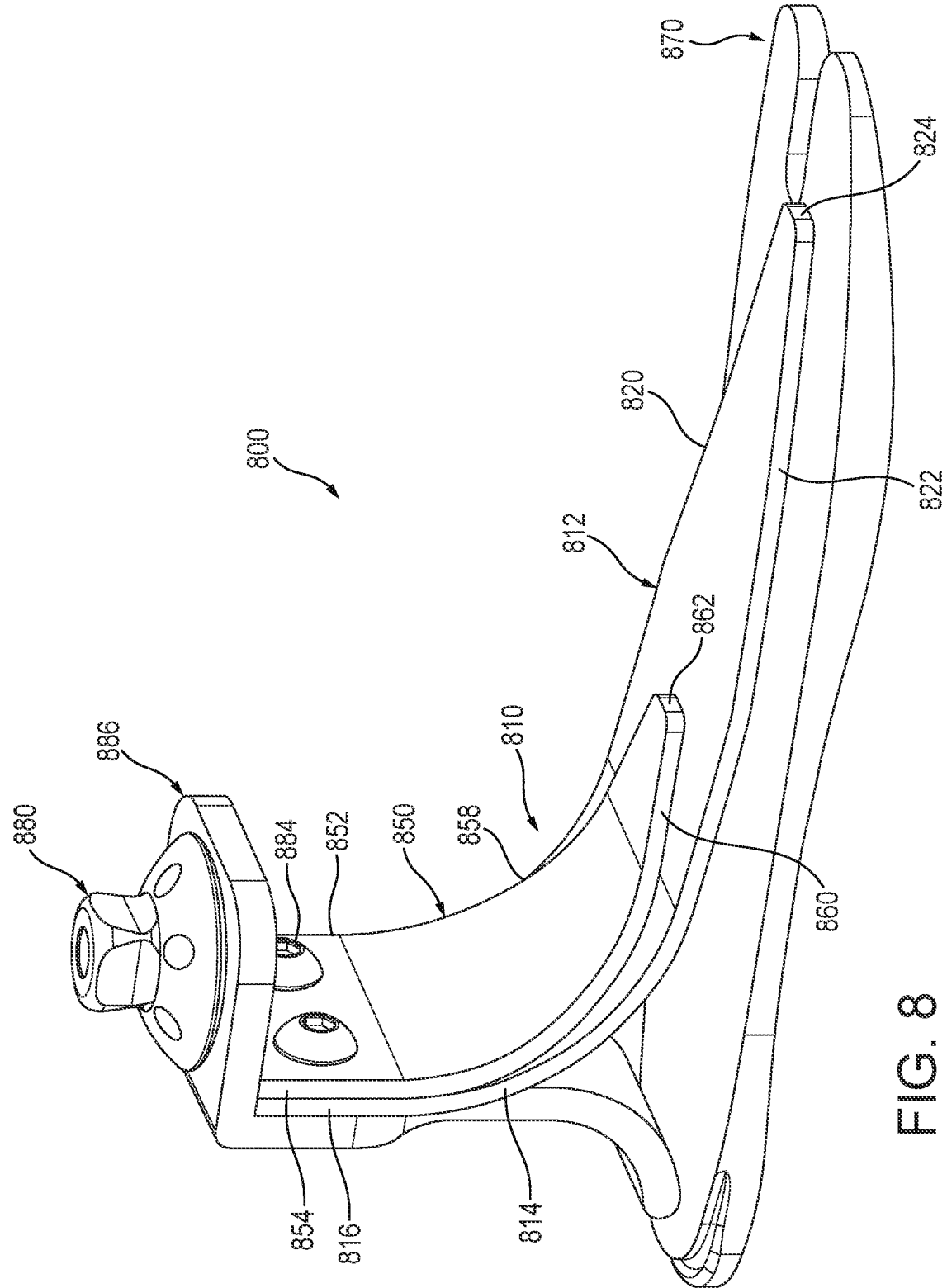
FIG. 8 is a perspective view of a prosthetic foot in which the composite spring component is constructed from stacked curvilinear beam elements.

To achieve compliant foot behavior in cases in which sufficient space is available for a prosthetic foot with a standard build height, concepts described herein may be applied to an alternate prosthetic foot with curvilinear beam elements, for example, as depicted in FIG. 8. As shown in FIG. 8, a prosthetic foot 800 includes a curved stacked plate composite beam, or spring component, 810 secured to a contoured bottom piece, or sole component, 870 and a shank connector (or pyramid connector or pyramid adaptor) 880 (which may be the same as shank connector 180 described above) connected to a connector mounting fixture, or bracket, 886 that is connected to the composite spring component 810, e.g., by fasteners 884.

Spring component 810 includes a bottom beam element 812 and a top beam element 850, although spring component 810 may be formed from more than two beam elements. Bottom beam element 812 includes a first portion 814 of its length and a second portion 820 of its length. First portion 814 includes an anchored end 816 at which the bottom beam element 812 is connected to the top beam element 850 and bracket 886 and may include a section or longitudinal extent of generally constant width. Second portion 820 includes a section or longitudinal extent 822 with a length-varying width, which may be linearly or approximately linearly tapered and may have a truncated tip 824 or a pointed tip (not shown).

Top beam element 850 includes a first portion 852 of its length and a second portion 858 of its length. First portion 852 includes an anchored end 854 at which the top beam element 850 is connected to the lower beam element 812 and the bracket 886 and may include a section or longitudinal extent of generally constant width. Second portion 858 includes a section or longitudinal extent 860 with a length-varying width, which may be linearly or approximately linearly tapered and may have a truncated tip 862 or a pointed tip (not shown).

In prosthetic foot 800, each of the stacked beam elements 812, 850 is curved in the sagittal plane. This curve allows the compliant beam elements to have a relatively long length while remaining within the anthropomorphic envelope. The long length of these beam elements allows them to deflect substantially when loaded, thereby allowing for compliant foot behavior. The long length of these beam elements is achieved through their curved shape. The benefits provided by their length is compounded with the benefits provided by the stacked beam compliant element, thereby providing a very compliant prosthetic foot design.

Figure 9:
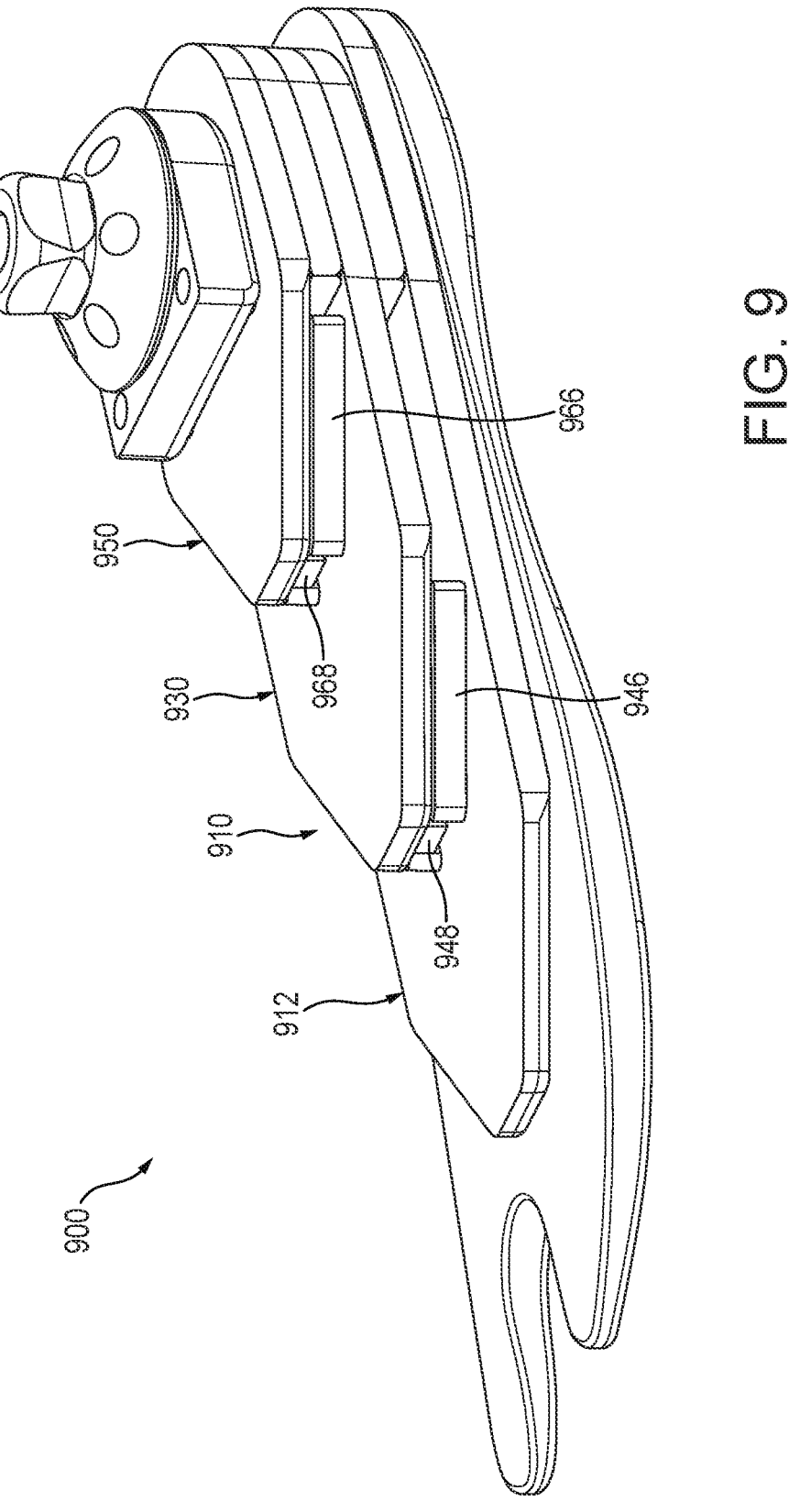
FIG. 9 is a perspective view of a prosthetic foot with stiffening spring component constructed from stacked beam elements (3 plates), which, when loaded, the beam elements sequentially contact one another, increasing the foot stiffness.
Figure 10:
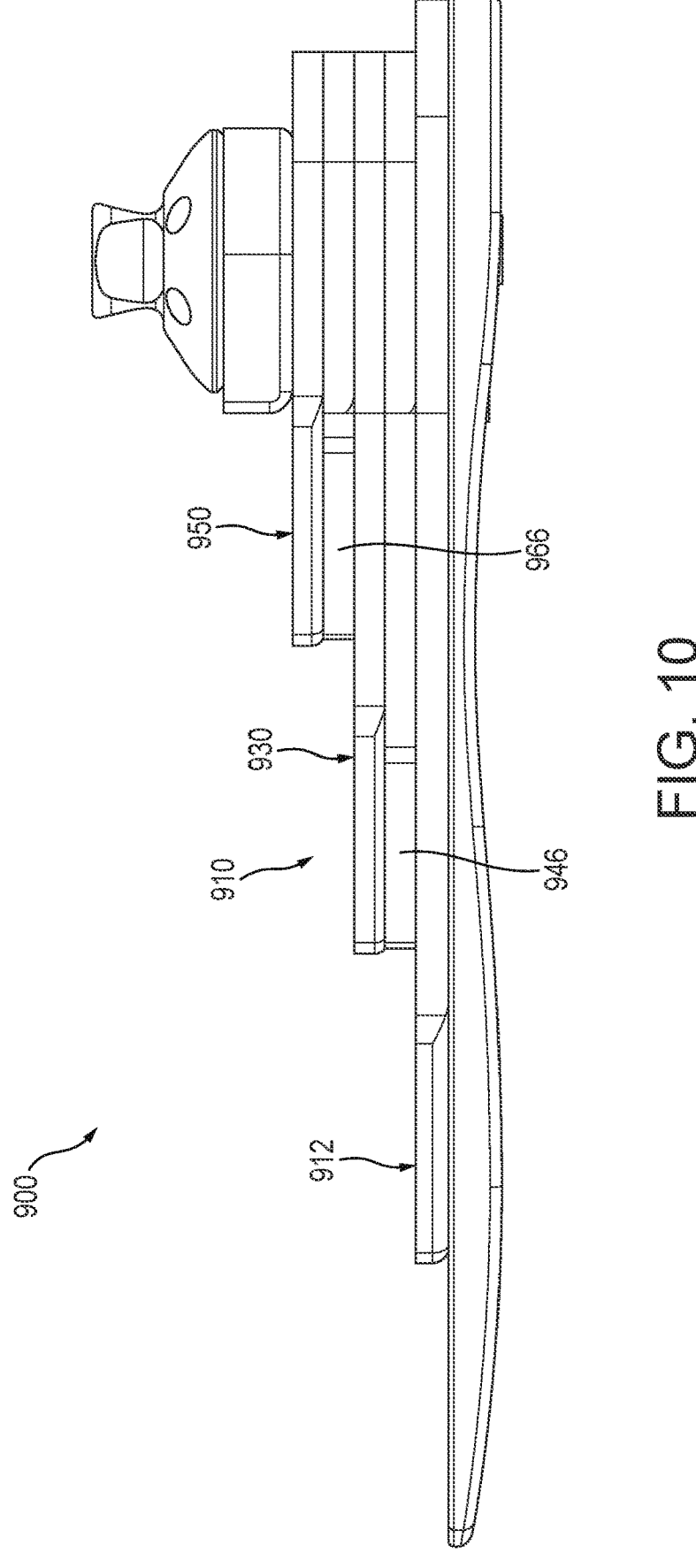
FIG. 10 is a side view of the prosthetic foot of FIG. 9.

As an example of a stiffening spring design (i.e. a spring for which the stiffness increases with applied load), gaps may be designed between the stacked beam elements of the composite spring such that, as loading increases, subsequent beam elements of the composite spring are engaged, thereby changing the stiffness properties of the composite spring as loading increases. FIGS. 9 and 10 illustrate an alternative prosthetic foot 900 with a composite spring component 910 having a bottom beam element 912, a middle beam element 930 and a top beam element 950 as described above. In addition, a compliant bumper 966 is placed between the top beam element 950 and middle beam element 930, and a compliant bumper 946 is placed between middle beam element 930 and bottom beam element 912. Additionally, a hard stop 968 is placed between top beam element 950 and middle beam element 930, and a hard stop 948 is placed between middle beam element 930 and bottom beam element 912. Hard stops 968 and 948 may be made from low-friction material. The height of each hard stop 968, 948 is less than the thickness of the associated compliant bumper 966, 946, respectively. As loading on the free end of the composite spring 910 increases, the compliant bumpers 946, 966 are compressed until a plate 930, 950 contacts the associated hard stop 948, 968, thereby engaging the next beam element of the composite spring. This process continues as the loading on the spring increases, subsequently engaging beam elements of the composite spring. As subsequent beam elements of the composite spring are engaged, the spring stiffness increases. In such a design, the stress is uniformly distributed across all of the beam elements of the composite spring only when the spring is substantially loaded, and all beam elements are in contact with one another i.e., directly or via a hard stop positioned between the beam elements.

Another approach to designing a stiffening composite spring component for a prosthetic foot is to shape the fixed end of the beam in a curved manner such that as the beam is loaded, the contact point between the beam and fixed end moves toward the free end of the beam, thereby stiffening the beam. This approach to designing stiffening springs was previously described, albeit not in applications involving prosthetic feet, in D. Spreemann, B. Folkmer, and Y. Manoli, "Realization of nonlinear hardening springs with predefined characteristic for vibration transducers based on beam structures," in MikroSystemTechnik Kongress, Darmstadt, Deutschland, 2011.

Figure 11:
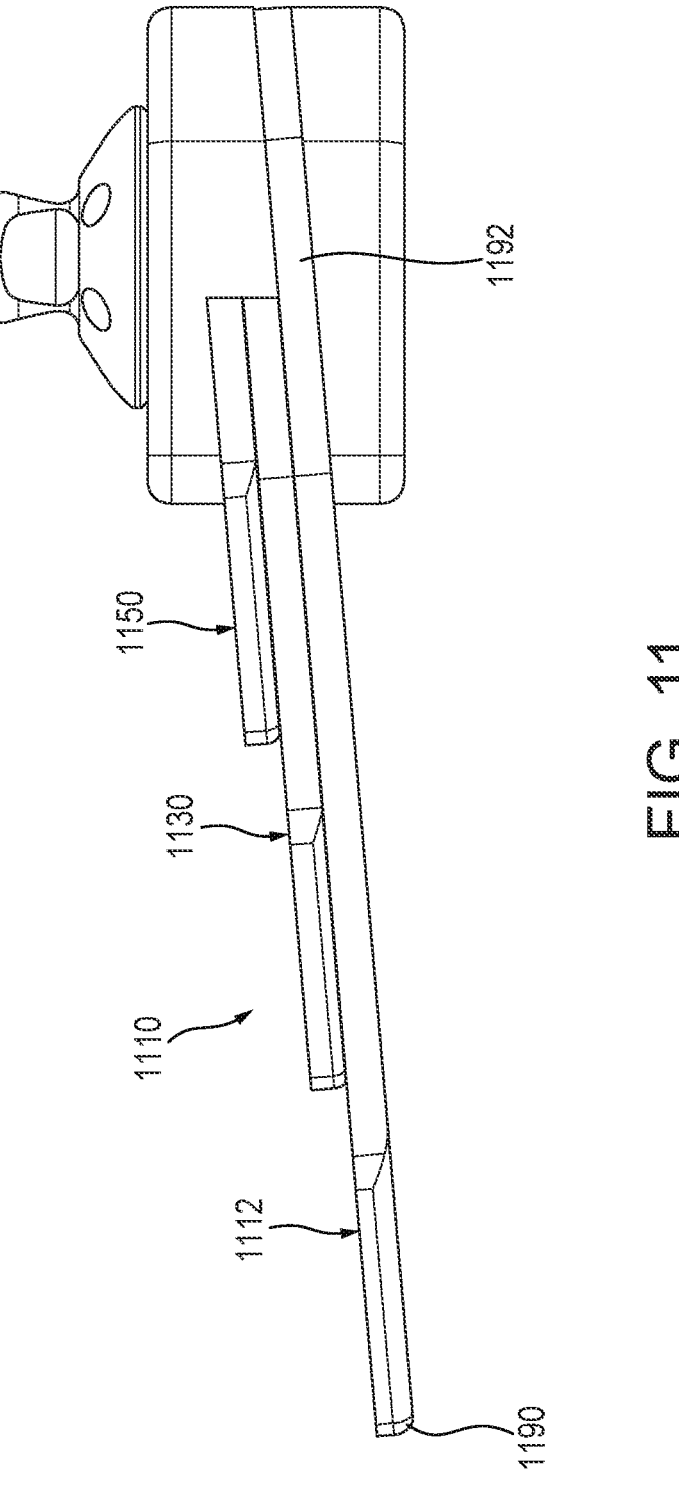
FIG. 11 is a side view of a prosthetic foot with a softening spring component constructed from stacked beam elements (3 plates), in which, when loaded, the beam elements deform in such a way so that the ground reaction force on the foot becomes more perpendicular to the spring component, thereby decreasing the foot's effective stiffness.

FIG. 11 illustrates an example of a softening (or weakening spring) composite spring component, or beam, 1110 including three beam elements 1112, 1130, 1150 (the spring component may have two or more beam elements) that is angled such that the free end tip 1190 of the composite spring component 1110 is positioned closer to the ground than the fixed end 1192 of the spring component 1110. In such an angled spring component, as the loading increases and the beam structure deforms, the loading is more perpendicular to the deformed beam. Such a beam's stiffness will decrease as the deflection of the beam increases.

Figure 12:
FIG. 12 is a perspective view of a prosthetic foot with a spring component constructed from stacked beam elements, each of which includes a transverse arch.

Another approach to design a spring component for a prosthetic foot with decreasing stiffness is to design the spring component as a beam with a transverse arch (arch in the frontal plane). FIG. 12 illustrates a prosthetic foot 1200 with a spring component, or beam, 1210 in which each stacked beam element 1212, 1230, 1250 (the spring component may comprise two or more beam elements) is transversely arched to create a composite beam of uniform strength and decreasing stiffness. In beam 1210 with a transverse arch, the arch structure provides high stiffness when the loading on the beam is low. However, as the loading increases, the arch shape is flattened, and the stiffness due to the arch geometry is reduced, thereby decreasing the stiffness of the overall beam structure.

Figure 15:
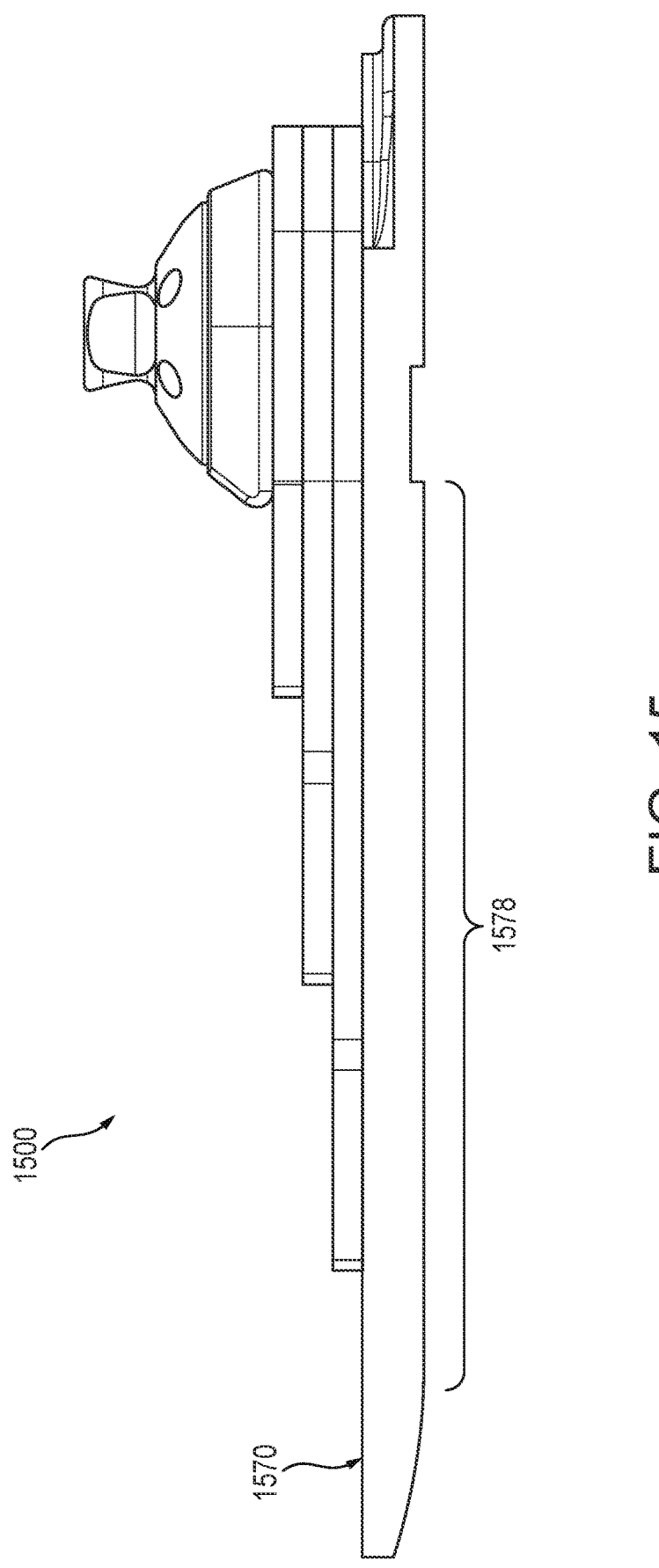
FIG. 15 is a side view of a prosthetic foot with decreasing stiffness and a contoured sole component with a long flat region.

Yet another approach to designing a softening spring for a prosthetic foot is simply to have a beam structure that contacts the ground along its entire length. In such a design, as a human user's center of pressure moves toward the toe during gait, the point of force application on the beam moves away from the fixed end of the beam. As such, the effective beam length increases, and the beam stiffness decreases as the center of pressure moves toward the toe during stance. Combinations of these various stiffening and softening spring design approaches may be utilized to design foot springs with custom stiffness profiles. During walking gait, a human's center of pressure progresses from heel to toe. If a beam structure is used as a prosthetic foot, and the beam lies flat on the ground during the stance phase of walking, the center of pressure will progress along the length of the beam during a stride. As the center of pressure progresses along the length of the beam, the effective cantilevered beam lengthens. Because long cantilevered beams are more compliant than short ones, this movement of the center of pressure across the beam tends to decrease the effective foot stiffness. FIG. 15 illustrates a prosthetic foot 1500 with decreasing stiffness by leveraging a contoured sole plate 1570 with a long flat region 1578 that will contact the ground during stance phase. Such a foot will achieve a softening behavior during walking through the natural movement of the user's center of pressure as described above.

Figure 13:
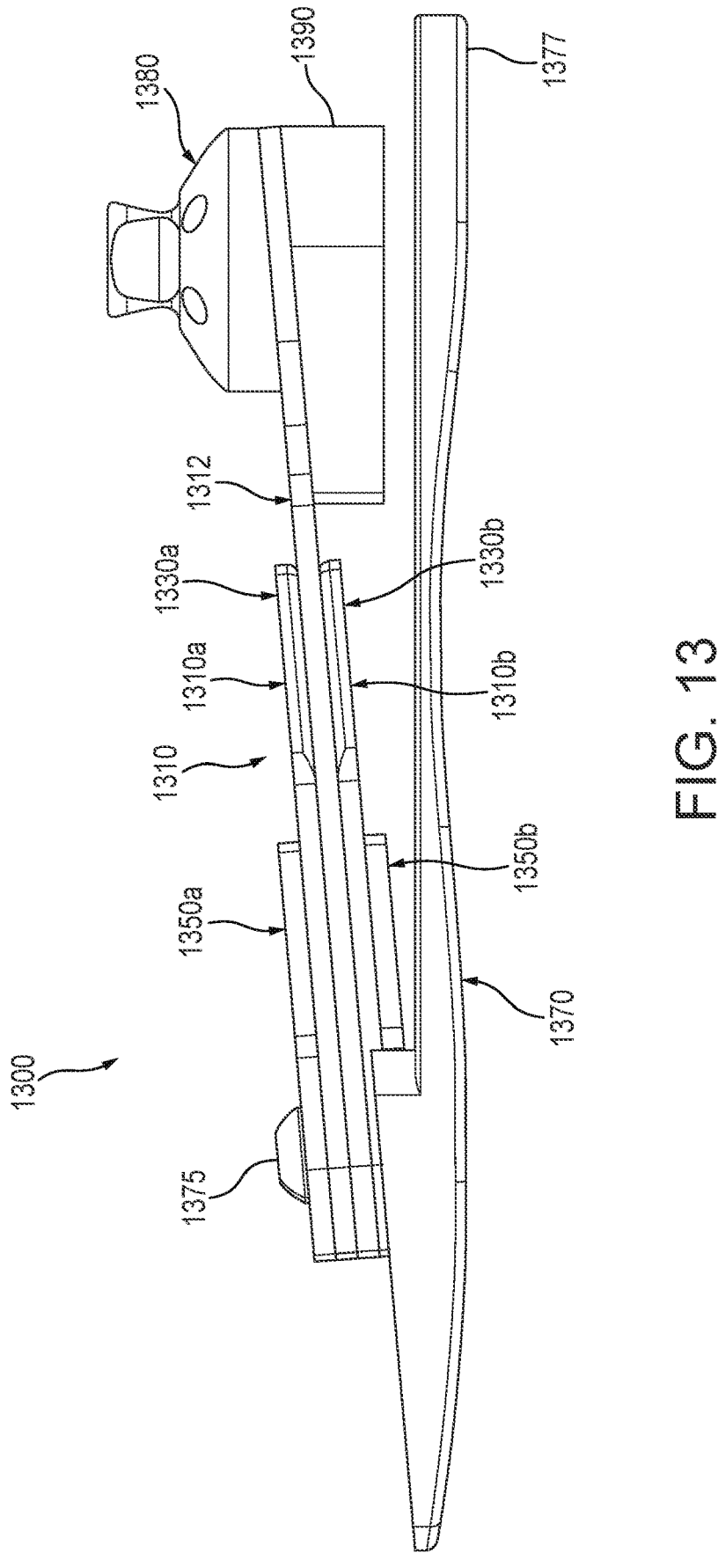
FIG. 13 is a side view of a prosthetic foot in which the composite spring component constructed from stacked beam elements is fixed to a toe end of the prosthesis, the shank member is then fixed only to a single layer of the composite spring component, and an elastomeric bumper is positioned under a heel section of the prosthetic foot.
Figure 14:
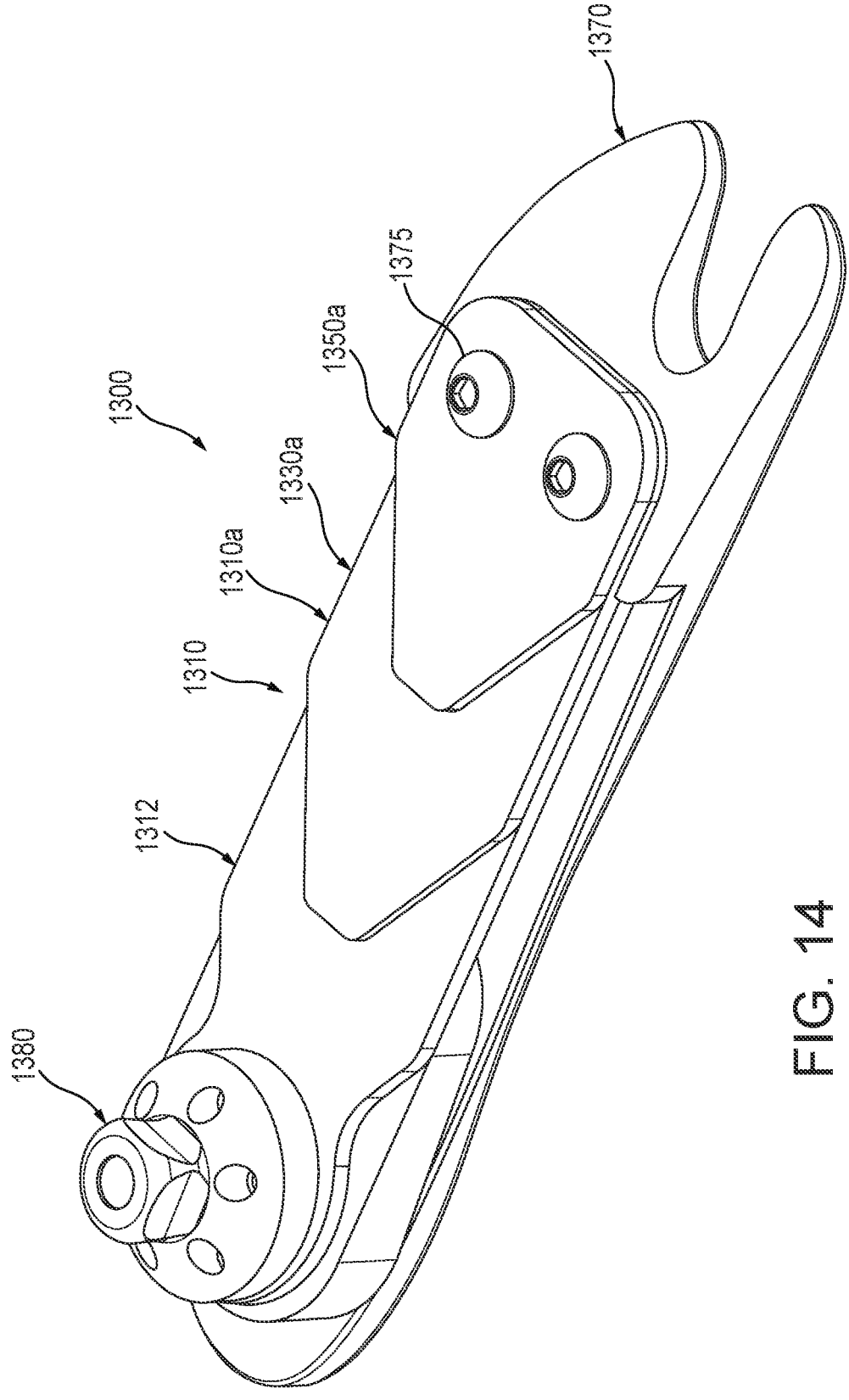
FIG. 14 is a perspective view of the prosthetic foot of FIG. 13.

In another example, the composite spring component may be fixed to the toe of the sole component, and the shank connector and shank may be connected to the free end of the spring component. An example of such a prosthetic foot 1300 is shown in FIGS. 13 and 14. Foot 1300 includes a stacked beam composite spring component 1310 that is fixed to a sole component 1370 at or near the toe end at 1375. As can be seen in the embodiment depicted in FIGS. 13 and 14, a shank connector 1380 may be fixed to the composite spring component 1310 near a heel end 1377 of the sole component 1370. This approach of fixing the spring component 1310 near the toe end 1375 of the sole component 1370 and affixing the shank connector 1380 to the free end of the spring component 1310 allows for different dynamic behavior depending on the direction of loading. Spring component 1310 includes a primary beam element 1312 extending the full length of the spring component 1310, a top intermediate beam element 1330a above the primary beam element 1312 and a bottom intermediate beam element 1330b below the primary beam element 1312, a top outer beam element 1350a above the top intermediate beam element 1330a, and a bottom outer beam element 1350b below the bottom intermediate beam element 1330. Accordingly, spring component 1310 comprises two composite spring components that act independently from each other: a first (upper) composite spring component 1310a comprising primary beam element 1312, top intermediate beam element 1330a, and top outer beam element 1350a and a second (lower) composite spring component 1310b comprising primary beam element 1312, bottom intermediate beam element 1330b, and bottom outer beam element 1350b. Each independent spring component 1310a, 1310b is engaged only when loaded in one direction. Upon application of an upward force at the toe end of the sole component 1370 (i.e., at or near 1375), the top beam elements 1330a, 1350a and the primary beam element 1312 bend, and upon application of a downward force to the shank connector 1380, the bottom beam elements 1330b, 1350b and the primary beam element 1312 bend. The top and bottom beam elements may be selected to be different to independently adjust stiffnesses.

As such, the prosthetic foot 1300 may be designed with distinct dynamic behavior appropriate for heelstrike and stance phases. When the foot is subject to a load tending to dorsiflex the foot, the first (upper) composite spring component 1310a is engaged, forming a particular stiffness. And when a load is applied that tends to plantarflex the foot, the second (lower) composite spring component 1310b is engaged, and the foot adopts a different stiffness according to selection of those engaged beam elements. This selective beam engagement approach may be used in conjunction with other components to provide a cushioned heelstrike behavior. For example, in FIGS. 13 and 14, an elastomeric bumper 1390 is placed under the primary beam element 1312 of the composite spring component 1310 to provide a shock absorption function during the plantarflexive loading at heelstrike.

In both discussed versions of uniform strength beams (i.e., the beam of constant width and varying thickness and the beam of varying width and constant thickness), the maximum stress is about the same at each point along the surface of the beam. As such, the stress in these beams of uniform strength is more evenly distributed across the beam relative to a simple cantilevered beam. This more evenly distributed stress provides a myriad of benefits when implemented as a prosthetic foot. Benefits of this stress distribution include increased durability, decreased foot stiffness, lower build height, increased energy storage, increased stiffness profile customization, and decreased device weight. It should be noted that the ideal uniform strength composite spring component, or beam, shapes may be changed slightly to create beams in which the maximum stress in the beam is approximately equal along the length of the beam. These small changes may be made to accommodate other practical aspects of prosthesis design.

Due to the more evenly distributed stress of the examples described herein, it is possible to create more durable prosthetic feet with the same physical behavior of feet designed using a simple cantilevered beam design approach. This increase in durability may extend the useful lifetime of a prosthetic device. The beneficial stress distribution properties of beams of uniform strength may also allow for the design of lower stiffness prosthetic feet within the same design envelope as a simple cantilevered beam type design. For example, a foot with a low build height may be designed with a lower stiffness than can be reasonably provided by a simple cantilevered beam style design. Similarly, the uniform strength beam foot design allows for the design of feet with lower build heights for the same stiffness behavior as simple cantilever beam style designs. This may allow for patients with long residual limbs to use devices with stiffness properties that they previously could not experience. Another significant benefit of the uniform strength beam-based foot design is that the more evenly distributed stress increases the strain energy density of the foot. Specifically, regions of the foot under high stress store significant strain energy. In the simple cantilever beam designs, only the fixed base of the foot stores significant energy (due to the stress concentration at the fixed end of a simple cantilever beam). However, in the uniform strength beam design, the maximum stress is experienced uniformly across the length of the beam, allowing more of the foot to store strain energy. Regarding prosthetic foot design, this high strain energy density allows for more energy storage and return for the patient as well as a smaller and lighter foot design.

In addition to the stiffness characteristics of a prosthetic foot, another important aspect of its function is the rollover shape that it provides. Rollover shape is the kinematic cam-like function of a foot. Specifically, rollover shape is defined as the path of the center of pressure as viewed from a reference frame fixed to the shank body member. In a compliant prosthetic foot the rollover shape is both a function of the stiffness of the foot as well as the shape of the region of the foot that contacts the ground. As such, it is possible to design a foot with a desired stiffness behavior and rollover shape through careful selection of the spring-like elements as well as the shape of the bottom of the foot. A desired rollover shape may be achieved through carefully designing the curved shape of the spring component.

Alternatively, the prosthetic foot may include a contoured bottom component coupled to the spring component. This contoured bottom component sits beneath the spring component and serves to create a contact shape between the spring component and the ground. This contoured bottom component may be shaped to affect the rollover shape of the prosthetic device. The shape of the contoured bottom component may be designed with knowledge of the spring component's stiffness properties to produce a desired rollover shape when loaded by a user.

The contoured bottom piece can also be utilized to modify the stiffness behavior of the prosthetic foot spring structure. For example, as shown in FIG. 6, the bottom surface 174 of the sole component 170, may include a toe pad 175 and a heel pad 177. A contoured sole component that only contacts the ground at the heel pad 177 and the bottom of the foot at the toe pad 175 constrains the beam to have forces applied only at the heel and ball of the foot, independent of the location of the center of pressure. In such a design scenario, the foot stiffness will remain relatively constant as the effective beam length is constant. As a counterexample, however, consider a contoured bottom piece that contacts the ground at the heel and then continuously from the middle of the foot to the toe (with a gap in contact between the heel and the middle of the foot). In such a design when the center of pressure progresses from heel to toe, the effective beam length will start to increase as the point of force application of the beam moves toward the toe. In this design, the stiffness will decrease as the center of pressure moves further toward the toe. These two examples indicate how the shape of the contoured bottom piece can be utilized to change the point of force application on the spring structure, thereby modifying its stiffness behavior.

Examples described herein also introduce the ability for the behavior of the prosthesis to be modified in a clinical setting to meet the needs of an individual patient. In the case of the prosthetic foot in which the spring component is a composite beam constructed of stacked beam elements (e.g., layered plates), both the stiffness properties and the rollover shape may be modified with minimal tooling. Specifically, the prosthesis stiffness may be decreased simply by decreasing the thicknesses of the stacked plates. In the case that the composite beam is constructed of layered flat plates, decreasing the thickness of the plates requires minimal tooling and may be accomplished by sanding, planing, or other methods. The stiffness of the prosthesis may also be modified to meet the needs of a patient by changing the number of stacked plates comprising the composite spring. In such an approach, plates may be cut out of a suitable material in a clinic and stacked to construct the composite foot spring. Additionally, plates of slightly different thicknesses may be stacked to easily change the prosthesis's stiffness properties. The rollover shape may also be modified through a combination of modifying the prosthesis stiffness as well as the shape of the contoured bottom component. If the contoured bottom component is made from an easilymachinable material such as Nylon, it may be easily modified with minimal tooling. Such an approach for modifying the behavior of the prosthesis within a clinical setting may allow for the behavior of prosthetic feet to be catered more precisely to the needs of individual patients relative to what is possible with conventional prosthetic feet.

In a prosthetic foot in which the spring component of the prosthesis is composed of a composite spring constructed from stacked beam elements, as described herein, the manufacturing cost of the prosthesis may be reduced relative to curved simple cantilever beam type prosthesis designs. Simple cantilever beam designs are typically curved to form the contour of the foot when viewed from the sagittal plane. These devices are also typically exhibit curves when viewed from other planes such as the frontal plane. This curved shape may be achieved by machining stock material or through a custom layup procedure for composite materials such as carbon fiber. Due to the curves present in multiple planes, the manufacturing process may involve multiple machining operations, jigs, or fixtures. This manufacturing process is generally both time consuming and expensive. In contrast, the spring elements of exemplary prostheses described herein are constructed from flat stock material cut into the appropriate two-dimensional shapes. As such, the manufacturing techniques required are substantially less costly and less time consuming. Manufacturing techniques that are appropriate for constructing such parts include water jet, wire electron discharge machining (EDM), and band saw, among others. These less costly manufacturing techniques may help to substantially reduce the production costs of the prosthetic foot.

Due to the ease and low-cost approach to manufacturing the composite spring components made of stacked flat plates and due to the high durability of a uniform strength beam design, the prosthetic foot examples described herein may be suitable for physically active patients. Specifically, feet consisting of composite springs constructed from stacked flat plates may be appropriate for patients such as physically active adults or children who exert high loads on prosthetic devices. The high durability allowed by the uniform strength design approach allows the spring component of the prosthetic foot to withstand many cycles at high loads. Additionally, due to the low manufacturing cost and effort associated with this design, if the spring component does fail, it may be replaced with relative ease and low cost. In the case of physically active patients, prosthetic feet may fail due to excessive loading. Replacing conventional prosthetic feet that have failed may be costly. Due to the simple design approach employed in the examples described herein, replacement spring components may be provided with relative ease and low cost. In the case of children requiring prosthetic limbs, not only do they exert large forces on the device (which may lead to device failure), children also grow quickly, necessitating larger prosthetic devices as time progresses. Replacement spring components may be provided with relative ease if a child breaks their prosthetic foot or outgrows it. This approach may allow for a child to simply replace spring components in their prosthetic foot as they grow. It may also be possible for these replacement spring components to be custom made in a clinical setting for a specific patient. The ability to simply interchange spring components in the prosthetic foot also allows for the possibility of a patient interchanging spring components for different desired physical behavior. A patient may wish to change the stiffness of their device as they adapt to using a prosthetic foot, as they switch between physical activities, as they gain weight, or for other reasons.

It should be noted that the examples described herein could be manufactured from a variety of different materials. By way of example, and not intended to be limiting, the beam elements of the composite spring component can be constructed from a material or materials with a capacity for high strain energy density such as fiberglass, carbon fiber, Kevlar, or Nylon. All beam elements may be made of the same material, or the spring component may be beam elements of two or more different materials sandwiched together.

A prosthetic foot as described herein may include one or more of the following characteristics.

A prosthetic foot comprising a shank member and a foot member; where the foot member may be comprised of a cantilevered spring component shaped so as to distribute the maximum stress approximately uniformly along its length when substantially loaded at the end of the cantilevered spring component.

The cantilevered spring component may be comprised of a series of layered flat or curvilinear beam elements with approximately constant thickness along their lengths; where the individual leaf springs are of varying lengths.

The layered beam elements may be interchanged with beam elements with different stiffness, length, or thickness properties.

The widths of the beam elements may change along their lengths.

The spring component may be cantilevered with a fixed end connected to a shank member and a free end of the spring component extending toward the toe portion of a sole component.

The spring component may be cantilevered with a fixed end connected to the sole component at the toe portion and the shank member connected to the free end of the spring component.

The stiffness properties of the spring component may be customized by modifying the number of layered beam elements and their respective shapes.

The stiffness properties of the spring component may be customized by modifying the thicknesses of the layered beam elements.

Friction forces between the layered beam elements may be minimized through the use of low friction coatings, elastomeric bearings, low friction materials, or other methods.

The stiffness of the cantilevered spring component may be designed to increase or decrease as loading at the end of the cantilever increases and the spring deflects.

The cantilevered spring component may include an arch in the transverse plane.

The prosthetic foot may include a contoured sole component, and the spring component is attached to the top of the contoured sole component.

The contoured sole component may be constructed and arranged to achieve a desired foot roll over shape.

The contoured sole component may be constructed and arranged to achieve a desired prosthetic foot stiffness behavior.

The roll over shape of the prosthetic foot may be customized by modifying the shape of the contoured sole component.

Concise Description of Various Embodiments

Embodiment 1—A prosthetic foot comprising:
a spring component; and
a sole component, wherein the spring component comprises two or more stacked beam elements, each beam element including, along the length of the respective beam element, a first portion and a second portion, wherein the second portion of the beam element includes an extent with a length-varying width, wherein the respective beam elements are fixed to each other and to the sole component at the first portions of the respective beam elements, and the second portions of the respective beam elements are laterally movable with respect to each other when the spring component deflects.

Embodiment 2—The prosthetic foot of embodiment 1, wherein the summed width of the two or more stacked beam elements increases approximately linearly from a second end of the spring component to a first end of the spring component.

Embodiment 3—The prosthetic foot of embodiment 1 or 2 wherein the two or more beam elements are of varying lengths.

Embodiment 4—The prosthetic foot of any one of embodiments 1-3 wherein the two or more stacked beam elements are flat plates.

Embodiment 5—The prosthetic foot of any one of embodiments 1-3 where the two or more stacked beam elements are curved laterally.

Embodiment 6—The prosthetic foot of any one of embodiments 1-3 wherein the two or more stacked beam elements are curved longitudinally.

Embodiment 7—The prosthetic foot of any one of embodiments 1-6 further comprising a shank connector connected to the spring component where the respective beam elements are fixed to each other and to the sole component and wherein a free end of the spring component extends toward a toe portion of the sole component.

Embodiment 8—The prosthetic foot of any one of embodiments 1-7 wherein the spring component comprises a cantilevered beam constructed and arranged so as to distribute maximum stress approximately uniformly along its length when loaded at a free end of the cantilevered beam.

Embodiment 9—The prosthetic foot of any one of embodiments 1-8 wherein the beam elements have approximately constant thicknesses along their lengths.

Embodiment 10—The prosthetic foot of any one of embodiments 1-9 further comprising a shank connector, wherein the respective beam elements are fixed to each other and to the sole component at or near a toe portion of the sole component, and the shank connector is connected to a free end of the spring component at or near a heel portion of the sole component.

Embodiment 11—The prosthetic foot of any one of embodiments 1-10 further including low friction coatings, elastomeric bearings, or low friction materials between overlapping beam elements.

Embodiment 12—The prosthetic foot of any one of embodiments 1-11, wherein each of the beam elements includes an arch in a transverse plane.

Embodiment 13—The prosthetic foot of any one of embodiments 1-12, wherein the extent of length-varying width of at least one of the beam elements is linearly tapered on opposed edges of the beam element.

Embodiment 14—The prosthetic foot of any one of embodiments 1-13, wherein the first portion of at least one of the beam elements includes a longitudinal extent of generally constant width.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the scope of the following appended claims.

The invention claimed is:

1. A prosthetic foot comprising:
a spring component; and
a sole component,
wherein the spring component comprises two or more stacked beam elements, each beam element including, along the length of the respective beam element, a first portion and a second portion, wherein the second portion of the beam element includes an extent with a length-varying width, wherein the respective beam elements are fixed to each other and to the sole component at the first portions of the respective beam elements, and the second portions of the respective beam elements are laterally movable with respect to each other when the spring component deflects, and wherein the summed width of the two or more stacked beam elements increases approximately linearly from a second end of the spring component to a first end of the spring component, wherein the two or more stacked beam elements are flat plates.

2. The prosthetic foot of claim 1 wherein the two or more beam elements are of varying lengths.

3. The prosthetic foot of claim 1 where the two or more stacked beam elements are curved laterally.

4. The prosthetic foot of claim 1 wherein the two or more stacked beam elements are curved longitudinally.

5. The prosthetic foot of claim 1 further comprising a shank connector connected to the spring component where the respective beam elements are fixed to each other and to the sole component and wherein a free end of the spring component extends toward a toe portion of the sole component.

6. The prosthetic foot of claim 1 wherein the spring component comprises a cantilevered beam constructed and arranged so as to distribute maximum stress approximately uniformly along its length when loaded at a free end of the cantilevered beam.

7. The prosthetic foot of claim 1 where the beam elements have approximately constant thicknesses along their lengths.

8. The prosthetic foot of claim 1 further comprising a shank connector, wherein the respective beam elements are fixed to each other and to the sole component at or near a toe portion of the sole component, and the shank connector is connected to a free end of the spring component at or near a heel portion of the sole component.

9. The prosthetic foot of claim 1, further including low friction coatings, elastomeric bearings, or low friction materials between overlapping beam elements.

10. The prosthetic foot of claim 1, wherein each of the beam elements includes an arch in a transverse plane.

11. The prosthetic foot of claim 1, wherein the extent of length-varying width of at least one of the beam elements is linearly tapered on opposed edges of the beam element.

12. The prosthetic foot of claim 1, wherein the first portion of at least one of the beam elements includes a longitudinal extent of generally constant width.

* * * * *